(12) United States Patent
Oka et al.

(10) Patent No.: US 7,172,860 B2
(45) Date of Patent: Feb. 6, 2007

(54) APPARATUS AND METHOD FOR MEASURING ACTIVITY SIGNALS OF BIOLOGICAL SAMPLES

(75) Inventors: Hiroaki Oka, Hirakata (JP); Nobuhiko Ozaki, Ikoma (JP); Hirokazu Sugihara, Katano (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 224 days.

(21) Appl. No.: 10/678,138

(22) Filed: Oct. 6, 2003

(65) Prior Publication Data

US 2004/0106139 A1    Jun. 3, 2004

(51) Int. Cl.
*C12Q 1/00* (2006.01)
(52) U.S. Cl. .......................................................... 435/4
(58) Field of Classification Search .............. 435/283.1
See application file for complete search history.

(56) References Cited

U.S. PATENT DOCUMENTS

| | | | |
|---|---|---|---|
| 5,183,744 A | | 2/1993 | Kawamura et al. |
| 6,682,649 B1 * | | 1/2004 | Petersen et al. .......... 205/777.5 |
| 2003/0080314 A1 | | 5/2003 | Nisch et al. |

FOREIGN PATENT DOCUMENTS

| | | |
|---|---|---|
| JP | 9-211010 | 8/1997 |
| JP | 9-289886 | 11/1997 |
| WO | WO 87/07295 | 12/1987 |
| WO | WO 99/34202 | 7/1999 |
| WO | WO 99/66329 | 12/1999 |
| WO | WO 01/25769 A2 | 4/2001 |

OTHER PUBLICATIONS

Masahito Tanabe, et al. "Saibo Shingo Keisoku-yo Micro Channel Array no Shisaku", Trial Micro Channel Array for Cell Activity Analysis, Aug. 30, 2001, pp. 257-261.

* cited by examiner

*Primary Examiner*—Christopher R. Tate
*Assistant Examiner*—Amanda P. Wood
(74) *Attorney, Agent, or Firm*—McDermott Will & Emery LLP

(57) ABSTRACT

The present invention provides an apparatus for measuring activity signals of a biological sample comprising: a measurement chamber (A) storing a target liquid containing a biological sample; a porous insulating substrate (5) provided with a measurement electrode (1) on at least one side; and a conveying device (8) which conveys the target liquid stored in the measurement chamber (A) and passes the target liquid through the porous insulating substrate (5) from the measurement electrode (1) side, wherein the conveying device (8) is operated to trap the biological sample contained in the target liquid onto the measurement electrode (1), so that the activity signals of the biological sample are measured through the measurement electrode (1). According to the apparatus, activity signals emitted from the biological sample can be detected easily, rapidly and accurately.

12 Claims, 15 Drawing Sheets

Fig.3
(A)
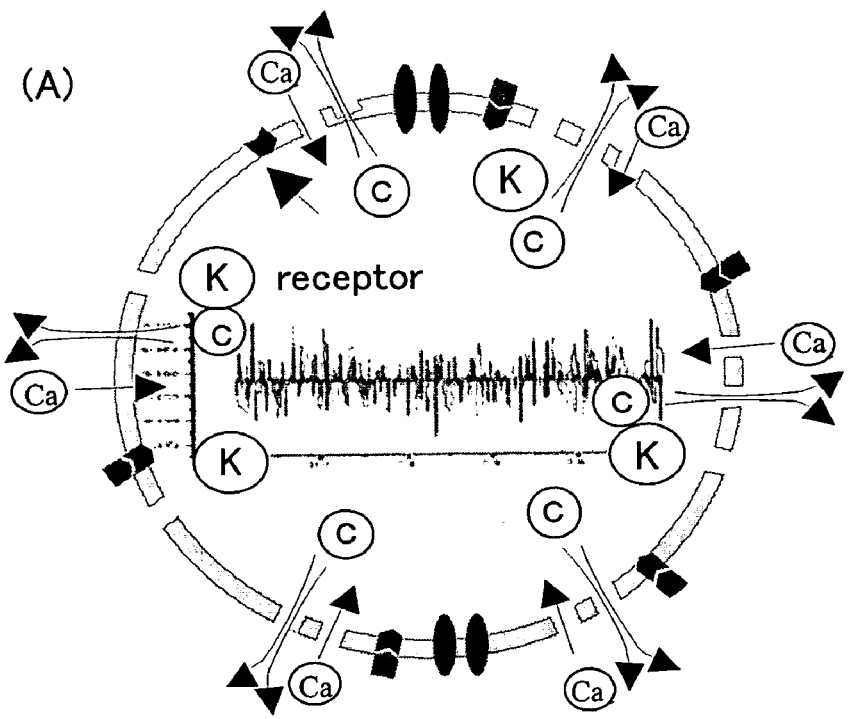
(B)
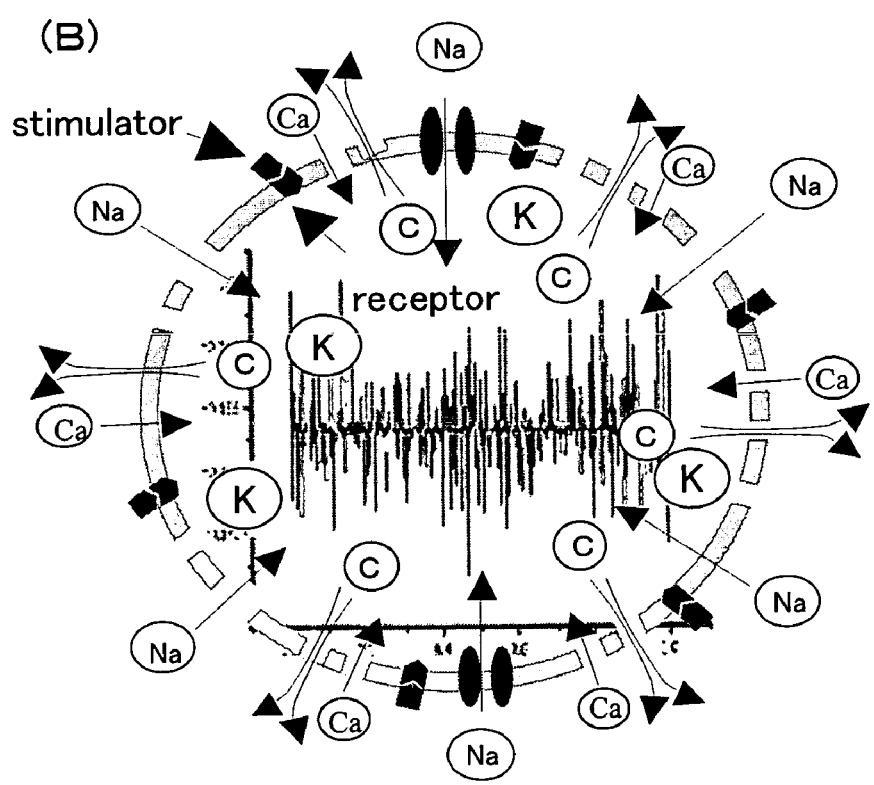

Fig. 6
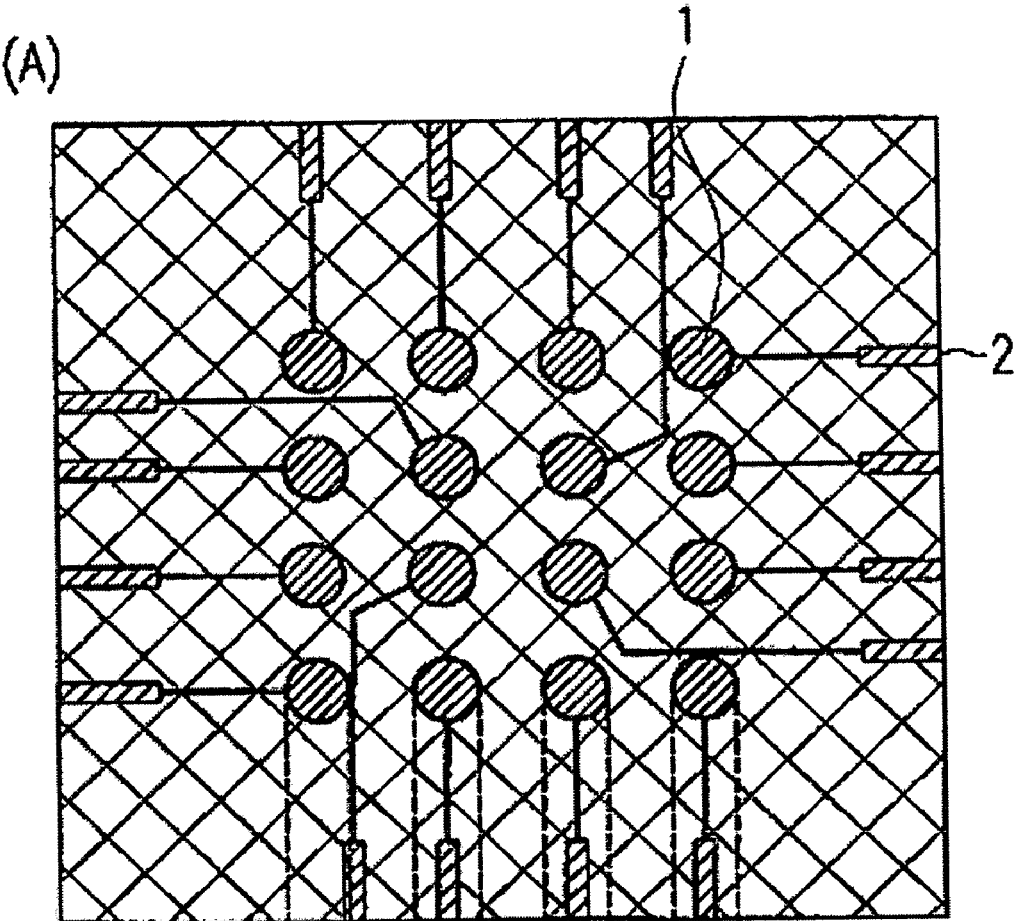
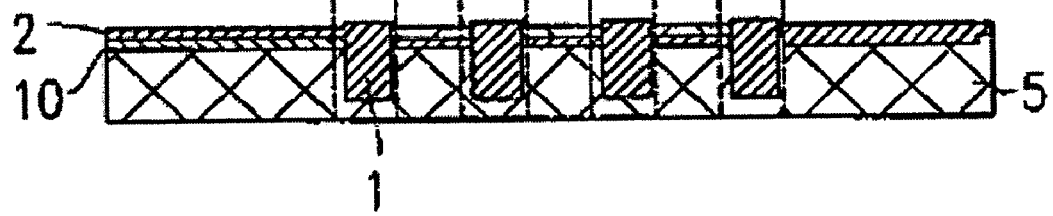

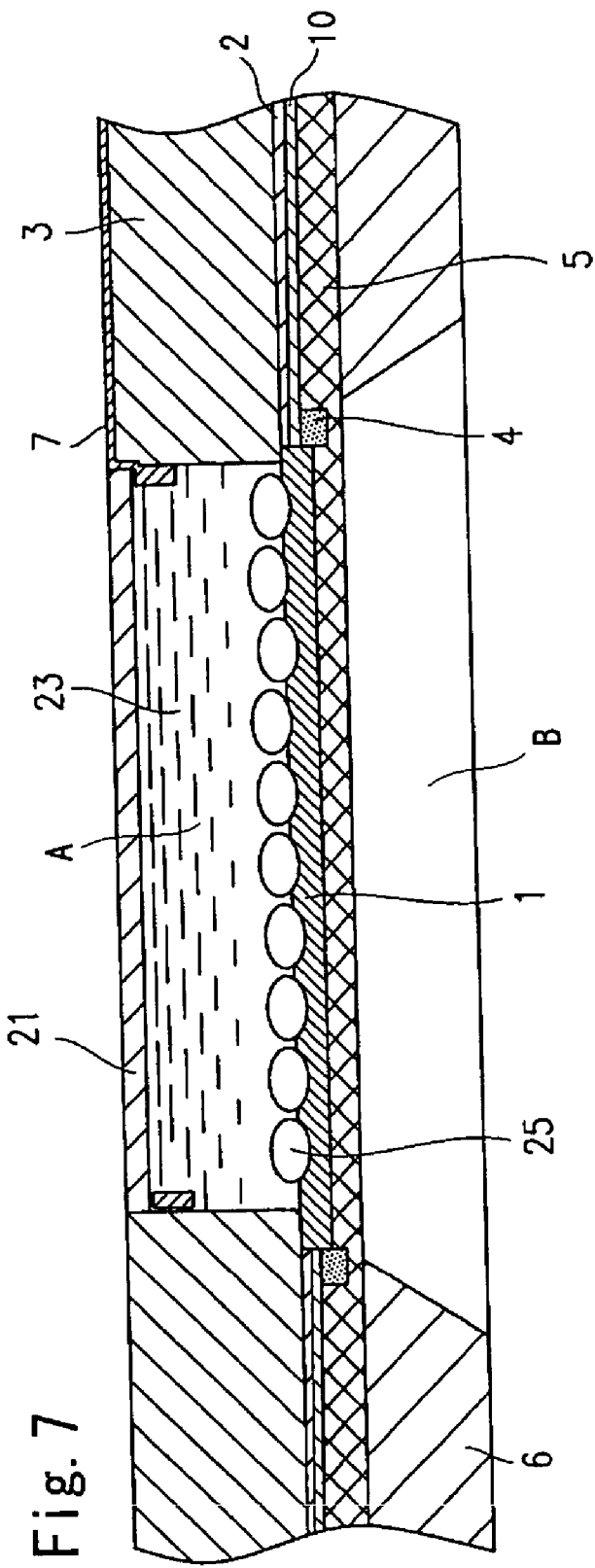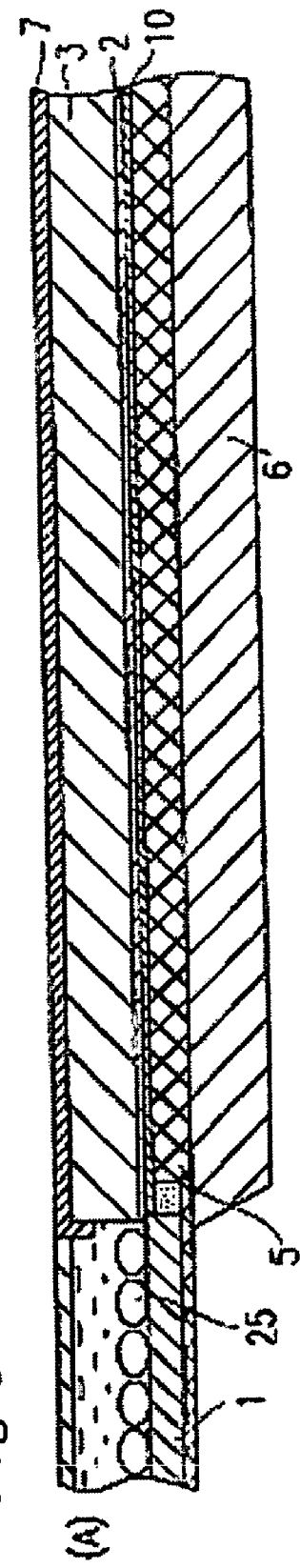

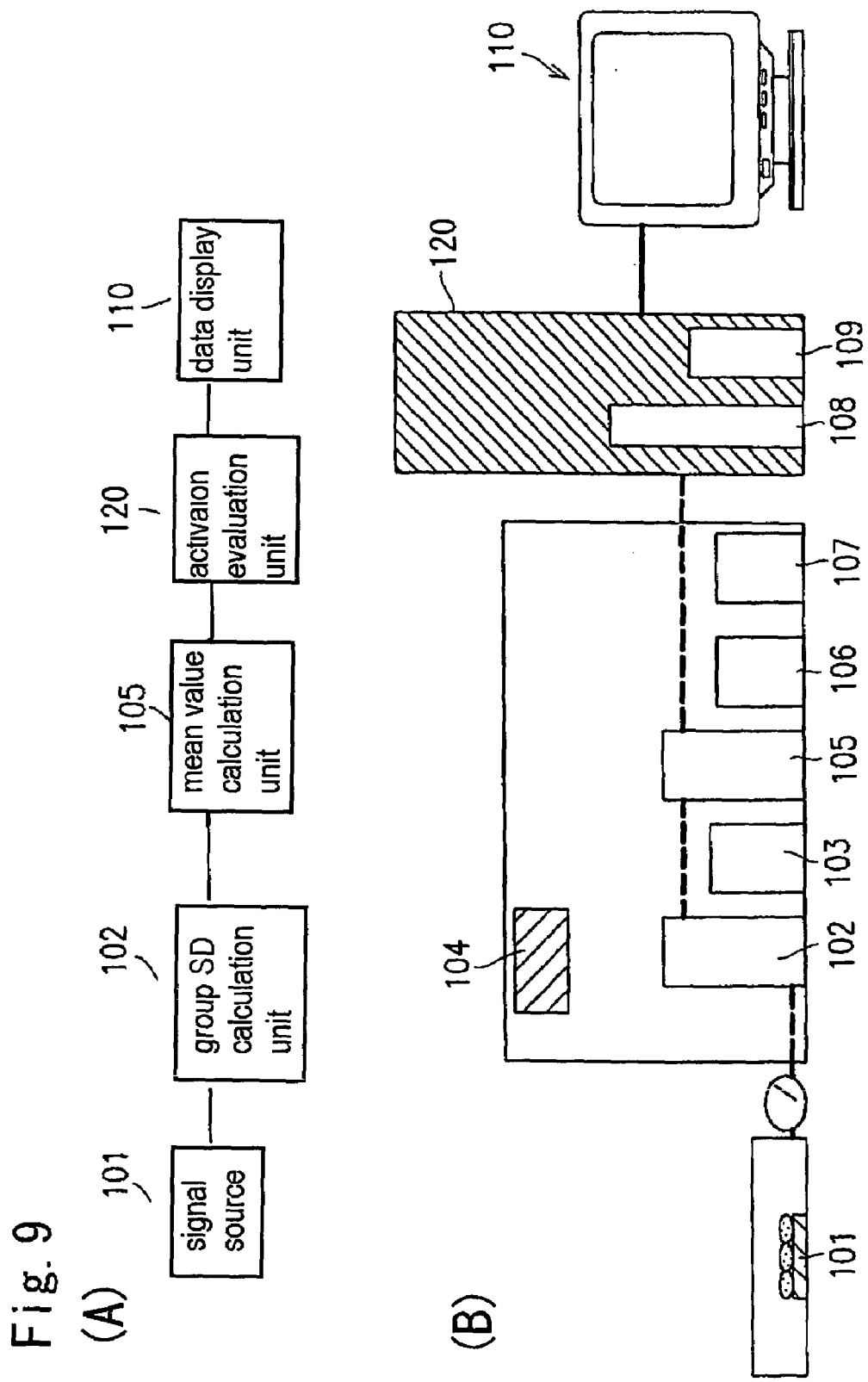

APPARATUS AND METHOD FOR MEASURING ACTIVITY SIGNALS OF BIOLOGICAL SAMPLES

TECHNICAL FIELD

The present invention relates to an apparatus and method for measuring activity signals emitted from a biological sample such as a cell or the like.

BACKGROUND OF THE INVENTION

Conventionally, physicochemical signals emitted in accordance with the activities of biological samples are taken into a measurement apparatus and measured as electrical signals, or as digital signals, such as the fluorescence intensity signals that are emitted from the biological sample when an indicator is incorporated therein. For example, when measuring the channel activation of a cell at the single channel level, an electrophysiology measurement apparatus provided with a microelectrode probe, such as a patch clamp, and an exclusive control device is used to obtain digital signals showing the quantity of electricity passing through the channel. The obtained digital signals are used to calculate the opening/closing periods, timing and frequency of the channel for measuring channel activation.

The patch clamp method employs a micro portion (patch) of a cell membrane attached to a tip of a micropipette so that ion transport via a single channel protein molecule can be electrically recorded with the microelectrode probe. Among cell biology techniques, the patch clamp method is one of the few methods that permit the real-time examination of the functions of a single protein molecule (e.g., "Molecular Biology of the Cell", 3rd edition, published by Garland Publishing Inc., New York, 1994, Japanese translation by Keiko NAKAMURA et al., pages 181 to 182, published in 1995 by Kyoiku Sha).

A fluorescent dye method is used for measuring the electrical activity of a cell in combination of an image processor and a luminous indicator or a fluorochrome that emits light depending on the concentration variations in a specified ion. For example, the ion mobility within a cell is monitored based on the fluorescence images of a cell taken by a CCD camera. According to the fluorescent dye method, the ion channel activation of an entire cell is generally determined by measuring the quantity of ions flowing into the cell by the fluorescence measurement method.

More specifically, the patch clamp method requires specialized techniques for preparing and handling a micropipette and takes a lot of time to measure one sample. Therefore, the patch clamp method is not suitable for the high-speed screening of various types of drug candidate compounds. In contrast, the fluorescent dye method permits the high-speed screening of various types of drug candidate compounds. However, the fluorescent dye method requires the step of dyeing the cell, which raises the problems of the high background caused by the dyestuff and the decolorization of the dyed cell with the passage of time, resulting in a lowered S/N ratio at measurement.

Methods for observing electrical and chemical variations in biological samples are disclosed in the prior art references of U.S. Pat. Nos. 2,949,845, 5,810,725, 5,563,067 and 5,187,069, Japanese Unexamined Patent Publication No. 1997-827318, and International Publication Nos. WO 01/25769, WO 98/54294, WO 99/66329 and WO 99/31503.

U.S. Pat. Nos. 2,949,845, 5,810,725 and 5,563,067 and Japanese Unexamined Patent Publication No. 1997-827318 disclose an integrated complex electrode and a measurement system using the same which are characterized by forming microelectrodes on a glass substrate using a photolithographic technique so as to extracellularly monitor the electrical changes of a cell with a multipoint.

International Publication No. WO 01/25769 discloses forming perforations on an insulating substrate, and arranging biological samples such as cells or the like containing ion channels at the perforations, so that a giga-seal is formed on the cell or the like and the insulating substrate surface. The thus configured substrate uses reference electrodes and measurement electrodes that are disposed at two areas separated by the giga-seal to measure the current that is generated when the ions pass through the ion channels.

U.S. Pat. No. 5,187,069 discloses a device which culture cells on an electrode and measures impedance changes to monitor cell proliferation.

International Publication No. WO 98/54294 discloses a device which causes a cell to adhere to a planar electrode for measuring electrical signals.

International Publication No. WO 99/66329 discloses a device for monitoring the activities of a cell on a porous material according to variations in resistance and impedance, and an assay method using the device.

International Publication No. WO. 99/31503 discloses a method using a substrate provided with perforations wherein a patch clamp is formed by trapping cells onto the perforations for use in measuring current variations.

Other prior arts of the present invention include Japanese Unexamined Patent Publication Nos. 1999-326166, 1993-157728 and 1987-73152.

DISCLOSURE OF THE INVENTION

An object of the present invention is to provide an apparatus and method for measuring activity signals of biological samples easily, rapidly and accurately.

The above object of the present invention can be achieved by an apparatus for measuring activity signals of a biological sample comprising: a measurement chamber storing a target liquid containing a biological sample; a porous insulating substrate provided with a measurement electrode on at least one side; and a conveying device which conveys the target liquid stored in the measurement chamber and passes the target liquid through the porous insulating substrate from the measurement electrode side. In the thus configured apparatus, the conveying device is operated to trap the biological sample contained in the target liquid onto the measurement electrode, so that the activity signals of the biological sample are measured through the measurement electrode.

Moreover, the object of the present invention can be achieved by a method for measuring activity signals of a biological sample comprising the steps of: injecting a target liquid containing a biological sample into a measurement chamber; trapping the biological sample onto a measurement electrode by conveying the target liquid from the measurement chamber and then passing the target liquid through a porous insulating substrate provided with the measurement electrode on at least one side; and measuring activity signals of the biological sample through the measurement electrode.

BRIEF DESCRIPTION OF THE DRAWINGS

FIGS. 3(A) and (B) schematically illustrate activities of biological samples (cells).

FIG. 6(A) is a plan view illustrating a porous insulating substrate of the apparatus shown in FIG. 4, and FIG. 6(B) is a cross sectional view illustrating the same.

FIG. 7 is a cross-sectional view partially illustrating the apparatus shown in FIG. 4.

FIG. 8 is another cross-sectional view partially illustrating the apparatus shown in FIG. 4.

FIGS. 9(A) and (B) are block diagrams schematically illustrating an apparatus for measuring activity signals emitted from biological samples according to Embodiment 3 of the present invention.

BEST MODE FOR CARRYING OUT THE PRESENT INVENTION

Hereinafter, the embodiments of the present invention will be described with reference to drawings.

(Embodiment 1)

Figure 1:
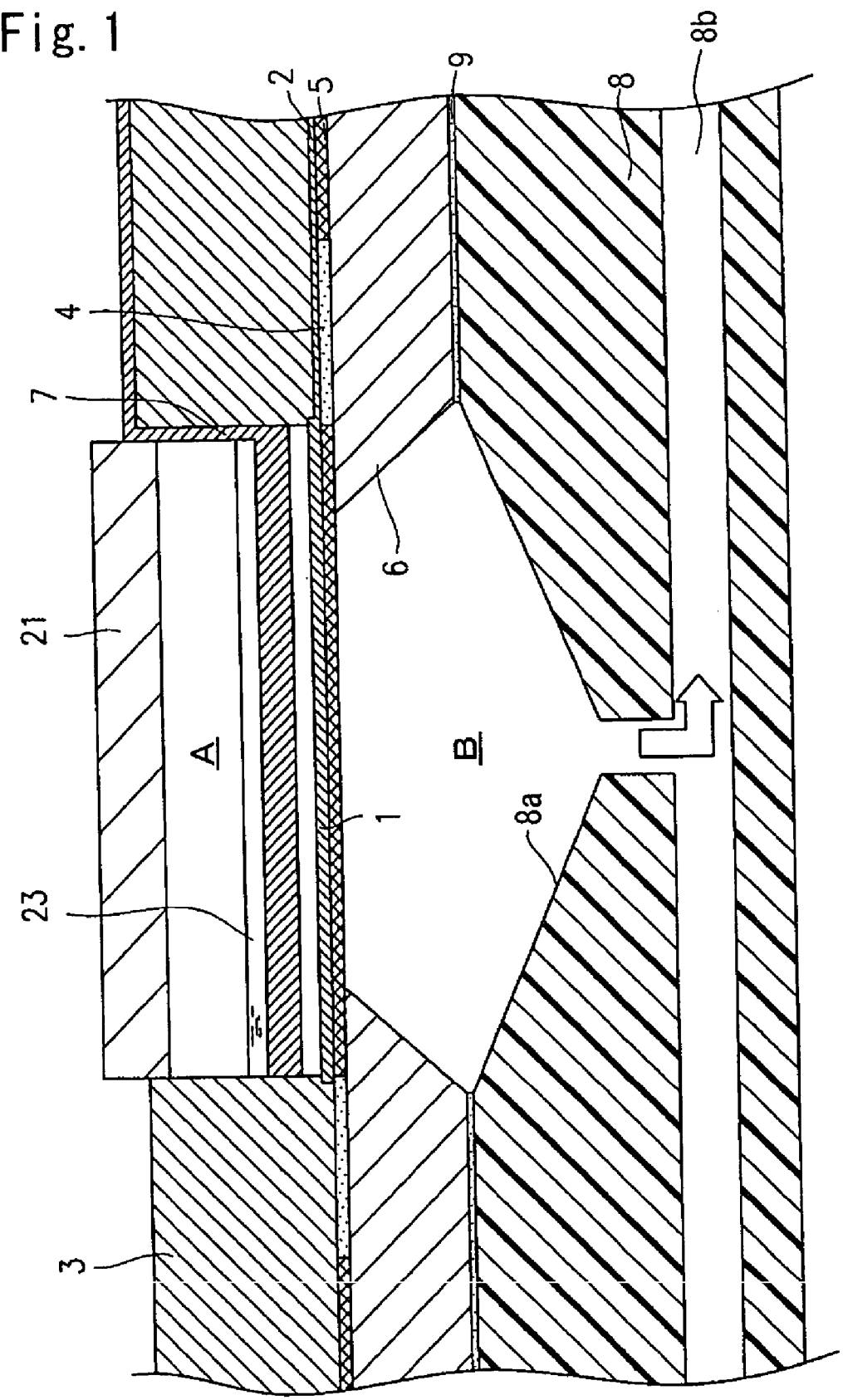
FIG. 1 schematically illustrates the configuration of an essential part of an apparatus for measuring the activity signals of biological samples according to Embodiment 1 of the present invention.

FIG. 1 schematically illustrates the configuration of an essential part of an apparatus for measuring the activity signals of biological samples according to Embodiment 1 of the present invention. The apparatus has a configuration such that a measurement electrode 1 for detecting physicochemical signals of biological samples such as a cell or the like is formed on the upper surface (the surface on which the biological sample is placed) of a porous insulating substrate 5, and a conductor 2 is derived from the measurement electrode 1. The physicochemical signal is a signal emitted from a biological sample such as a cell or the like. More specifically, it is a signal emitted from a specific portion of a measurement target, such as the ion channel of a cell, or a signal which varies due to specific events occurring in the measurement target, such as the activation of the ion channel or receptor of a cell in reaction to a drug.

A nylon mesh is employed as the porous insulating substrate 5 in this embodiment. However, the porous insulating substrate 5 is not limited thereto and cellulose mixed ester, hydrophilic polyvinylidene difluoride, hydrophobic polyvinylidene difluoride, polytetrafluoroethylene, polycarbonate, polypropylene, polyethylene terephthalate, etc., may be used. More specifically, Isopore (made of polyethylene terephthalate, product of Millipore) or Omnipore (made of polytetrafluoroethylene, product of Millipore) is preferably used. Generally, a porous insulating substrate 5 having a pore diameter of not less than 1 μm but not more than 1,000 μm and a thickness of not less than 1 μm but not more than 10,000 μm is selected. Typically, a porous insulating substrate having a pore diameter of 5 μm and a thickness of 10 μm can be used. However, a porous insulating substrate having a thickness of 100 μm or more is preferably used.

The measurement apparatus is obtained as described below. A measurement electrode 1 and a conductor 2 are initially formed on the porous insulating substrate 5, preferably by sputtering a conductive material. According to this embodiment, gold is used as the conductive material and plasma is generated by a high frequency between a pair of electrodes under a low vacuum in the presence of an inert gas such as argon. The gold is repelled from the cathode by ion energy, and forms on the porous insulating substrate which is positioned on an anode opposite to the cathode. The electrode and the conductor can be also formed by a vacuum evaporation method or a printing method instead of the sputtering method. Platinum, copper, silver, a combination of silver and silver chloride, or a combination of platinum and platinum black can be used instead of gold as the conductive material. Moreover, a conductive material containing a conductive plastic can be used instead of metallic materials.

The measurement electrode 1 is preferably formed by sputtering without a mask so that the electrode material is infused deeply into the porous insulating substrate 5. In contrast, the conductor 2 is preferably formed by pre-covering the porous insulating substrate 5 with a mask (not shown) for patterning so that the conductive material is prevented from infusing deeply into the porous insulating substrate 5.

In this embodiment, the measurement electrode 1 is formed in a disk shape, but it may take any shape depending on the measurement target. The measurement electrode 1 is not particularly limited in size, but in this embodiment, it has approximately the same horizontal cross-section area as a measurement chamber A, which will be described later.

As described above, the measurement electrode 1 and the conductor 2 are formed on the porous insulating substrate 5. Thereafter, the porous insulating substrate 5 is clamped between a cell separating unit 3 and a support 6. The cell separating unit 3 and the support 6 are each provided with an aperture, and the centers of the aperture of the cell separating unit 3, the measurement electrode 1 formed on the porous insulating substrate 5, and the aperture of the support 6 are disposed so as to be approximately in alignment. Thus, the aperture wall of the cell separating unit 3 and the porous insulating substrate 5 define the measurement chamber A (corresponding to the entire space of the aperture formed in the cell separating unit 3 in FIG. 1). The cell separating unit 3 and the support 6 are fixed to an adhesive layer 4 containing adhesive, which is provided around the aperture. The adhesive layer 4 preferably has easy peelability and is watertight. For example, one-component RTV rubber (diacetate-type) KE42T (product of Shin-Etsu Chemical Co., Ltd.) can be used.

A reference electrode 7 is disposed at a side wall of the measurement chamber A, and is immersed in a target liquid 23 which is stored in the measurement chamber A. The reference electrode 7 provides a reference electric potential for detecting the activity signals of the biological samples to be measured, and is composed of, for example, Ag—AgCl. The target liquid 23 includes a DMEM culture medium. The cells to be cultured include animal-derived cells.

The measurement chamber A is covered with a lid 21, which prevents the target liquid 23 from evaporating. The lid 21 is not necessarily required, depending on the type and the measurement conditions of the target liquid 23, and thus a configuration with no lid 21 is also acceptable.

Subsequently, a suction line attachment 8 is fixed to a side of an under surface of the support 6 with an adhesive layer 9 sandwiched therebetween. The suction line attachment 8 consists of a suction unit 8a tapering from the bottom to the top and a suction line 8b for connection to the suction unit 8a. The suction unit 8a is positioned to be approximately in alignment to the aperture of the support 6. Thus, a suction chamber 8 is delimited by the porous insulating substrate 5, the aperture wall of the support 6 and the inner wall of the suction unit 8a. The suction line attachment 8 functions as a conveying device for sucking and conveying the target liquid 23, and is connected to a suction pump (not shown). The apparatus for measuring the activity signals of biological samples can be thus configured.

Hereinafter, a method for measuring the activity signals of biological samples using the above-mentioned apparatus will be described. Initially, the target liquid 23, such as a cell medium or the like, is injected into the measurement chamber A. The amount of the target liquid 23 is, for example, 50 µl.

When there is no suction force acting on the suction unit 8a, the amount of the target liquid 23 that drops through the porous insulating substrate 5 to the suction chamber B is very small. Generally, the amount is one-fiftieth or less of the total target liquid 23 stored in the measurement chamber A.

Figure 2:
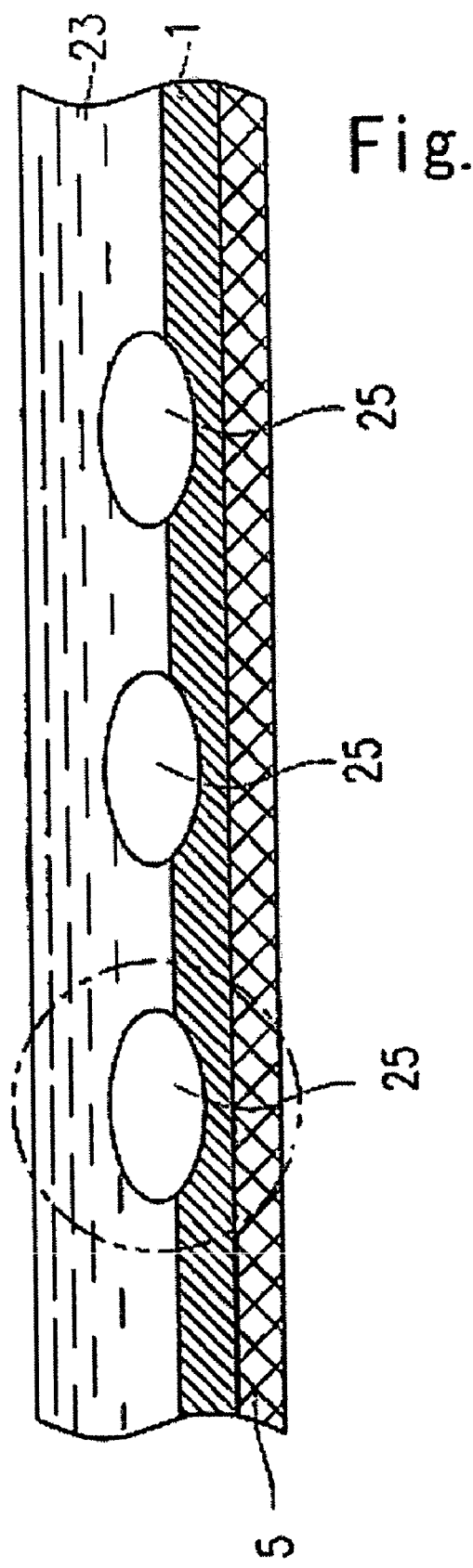
FIG. 2 is an enlarged view of the essential parts of the apparatus shown in FIG. 1.

Subsequently, the suction pump (not shown) is used to suck the target liquid 23 stored in the measurement chamber A. When the suction chamber B is depressurized, the target liquid 23 passes through the porous insulating substrate 5, and subsequently flows through the suction line 8b via the suction chamber B in the direction shown by the arrow. In contrast, biological samples 25 contained in the target liquid 23 cannot pass through the porous insulating substrate 5, and are thus adsorbed to the measurement electrode 1 as shown in FIG. 2. Activity signals emitted from the biological samples can be detected as an electrical potential difference generated between the measurement electrode 1 and the reference electrode 7. For example, when the biological sample 25 is a cell in a static state as shown in FIG. 3 (A), the opening and closing of the ion channels are in a state of equilibrium and conductance varies only slightly between channels so the change in generated voltage is small, potential amplitude in the vicinity of a cell membrane is approximately uniform. In contrast, as shown in FIG. 3(B), when the cell is in an active state, the opening and closing of the ion channels are not in a state of equilibrium, and conductance varies greatly between channels so the change in generated voltage is large, and the potential amplitude in the vicinity of the cell membrane is not uniform. Therefore, cell activity can be determined on the basis of time-series variations in the detected electrical potentials.

After measuring, the inside of the apparatus is washed by feeding a cleaning solution, such as a physical saline, into the measurement chamber A while operating the suction pump (not shown). The porous insulating substrate 5 may be replaced, if necessary, before a different target liquid 23 is injected into the measurement chamber A. Thus, the activity signals of biological samples can be successively measured on various solutions containing drug candidate compounds.

As described above, according to the measurement method of the present invention, the target liquid 23 is simply supplied to the measurement chamber A and is sucked via the suction line attachment 8. Thus, the biological samples 25 can be adsorbed to the measurement electrode 1, to increase contact resistance, resulting in improved signal detection sensitivity. Moreover, the suction line attachment 8 expedites the processes of renewing the target liquid 23 and cleaning. Consequently, the activity signals of biological samples can be measured easily, rapidly and accurately.

(Embodiment 2)

Figure 4:
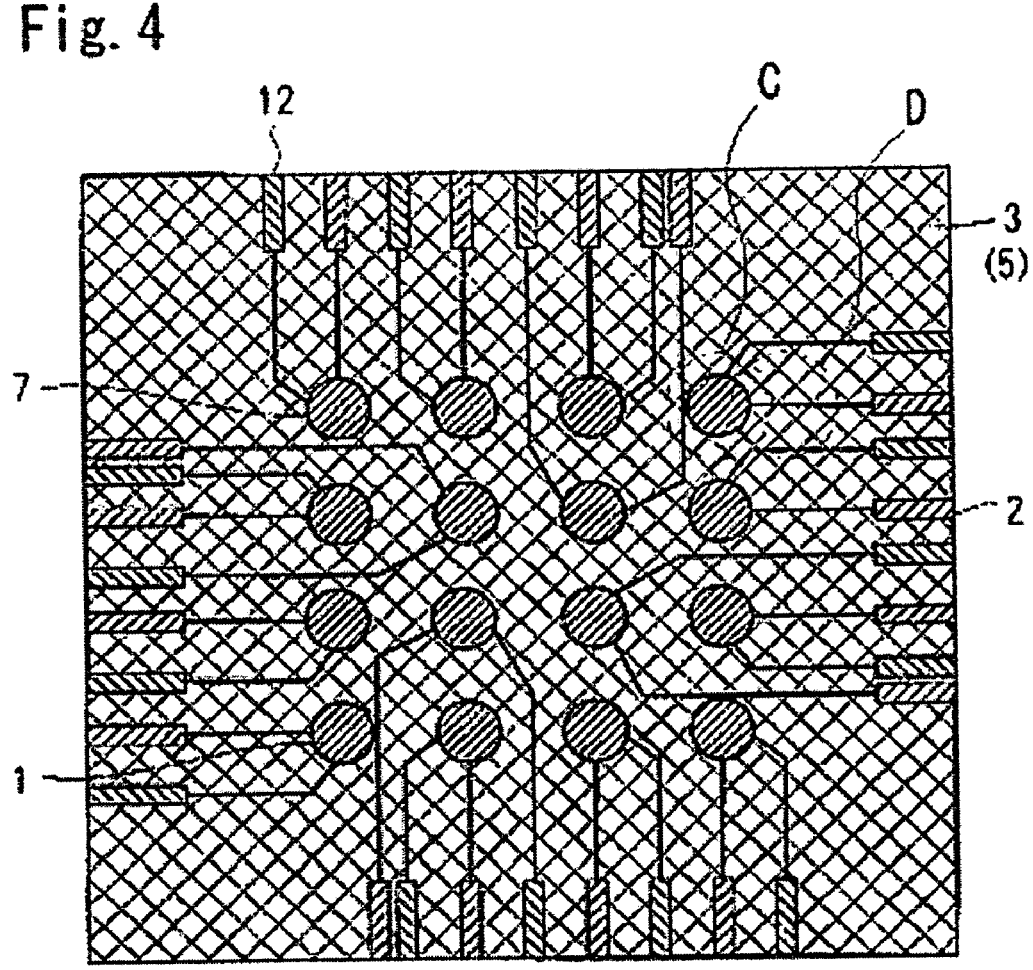
FIG. 4 is a plan view schematically illustrating an apparatus for measuring activity signals emitted from biological samples according to Embodiment 2.

FIG. 4 is a plan view schematically illustrating an apparatus for measuring the activity signals of biological samples according to Embodiment 2 of the present invention. The apparatus according to Embodiment 2 is obtained by arranging in a matrix 16 of the measurement electrodes 1 employed in the apparatus of Embodiment 1 shown in FIG. 1. In the present embodiment, the diameter of each measurement electrode 1 is set to be 2 mm, and the space between adjacent respective measurement electrodes 1 is set to be 1 mm. The measurement electrodes 1 are not particularly limited to the number, arrangement, size, shape and the like of this embodiment, but the measurement electrode 1 is preferred to have, for example, an area of not less than 1 $\mu m^2$ but not more than 1 $cm^2$, an approximately circular or rectangular shape, has a space of not less than 10 but not more than 10,000 µm between adjacent measurement electrodes 1, to be arranged in a matrix. In this embodiment, the same parts are designated by the same numerals as in Embodiment 1, and thus the detailed descriptions are omitted.

In FIG. 4, the measurement electrodes 1 and the conductors 2 connected thereto are arranged on the front side of the porous insulating substrate 5. The porous configuration may be destroyed by using the heat or laser beams between a plurality of conductors 2 on the front side of the porous insulating substrate 5 to thereby further increase the insulation. The reference electrodes 7 and the conductors 12 connected thereto are individually arranged on the inner wall and the top surface of the aperture of the cell separating unit 3 to correspond to each measurement electrode 1. The cell separating unit 3 is usually composed of a transparent material.

Figure 5:
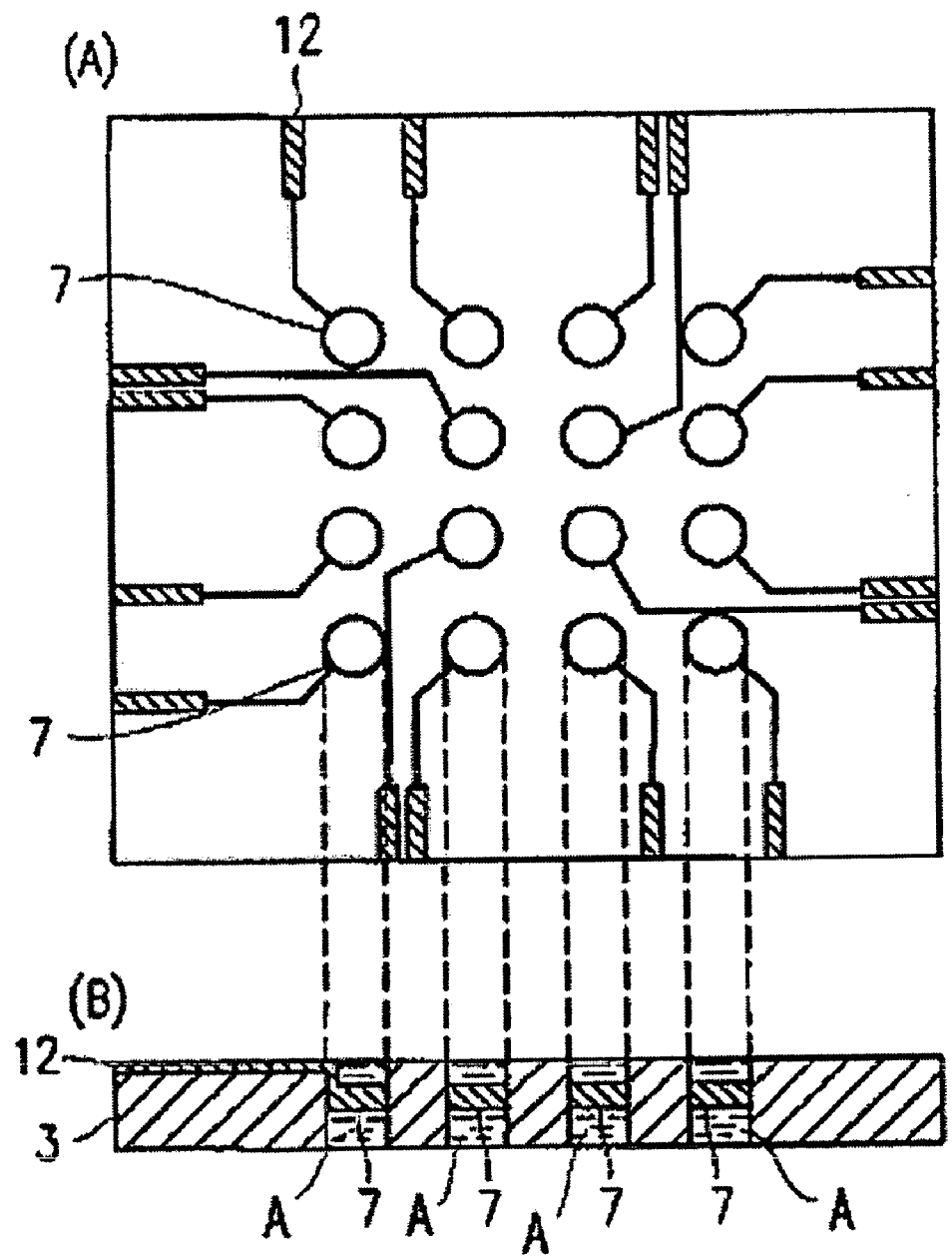
FIG. 5(A) is a plan view illustrating a cell separating unit of the apparatus shown in FIG. 4.
FIG. 5(B) is a cross sectional view illustrating the same.

FIG. 5(A) is a plan view and FIG. 5(B) is a cross-sectional view with reference to the cell separating unit 3. FIG. 6(A) is a plan view and FIG. 6(B) is a cross-sectional view with reference to the porous insulating substrate 5. As shown in FIG. 5, a measurement chamber A is formed at each aperture of the cell separating units 3, in which a plurality of measurement electrodes (not shown) are disposed. As shown in FIG. 6(B), the measurement electrodes 1 are formed by sputtering conductive materials without a mask so that the material is infused into the inside of the porous insulating substrate 5. Alternatively, the conductor 2 is formed by sputtering the conductive material through a mask layer 10 formed on the top side of the porous insulating substrate 5 so that the material is prevented from infusing into the inside of the porous insulating substrate 5. FIGS. 7 and 8 are cross sectional views partially illustrating the apparatus shown in FIG. 4. FIG. 7 is an enlarged view of area C. FIG. 8 is an enlarged view of area D. The biological samples 25 of a cell or the like contained in the target liquid 23 are sucked by the suction line attachment (not shown) and adsorbed to the measurement electrode 1 in the same manner as in Embodiment 1. The suction line attachment A is provided with a plurality of suction units (corresponding to reference numeral 8a in FIG. 1) corresponding to the respective measurement electrodes 1, and can cause the biological samples 25 to simultaneously adsorb to the respective measurement electrodes 1 via the common suction line (corresponding to reference numeral 8b in FIG. 1). Thus, the activity signals of the biological samples can be measured under various conditions in a short time. The timing for the adsorption of the biological samples 25 to the respective measurement electrodes can be varied by providing an individual suction line to each measurement electrode 1 instead of the common suction line.

(Embodiment 3)

FIG. 9 is a block diagram schematically illustrating a configuration of the apparatus for measuring the activity signals of biological samples according to Embodiment 3. The apparatus employs the apparatus of Embodiment 1 as a measurement unit (a signal source) 101, and has a function for processing electrical signals detected by the measurement unit 101. As shown in FIG. 9(A), the apparatus is provided with a group SD (standard deviation) calculation unit 102, a mean value calculation unit 105, an activation evaluation unit 120 and a data display unit 110. According to the group SD calculation unit 102, the standard deviation of one group consisting of a predetermined number of samples is calculated on the basis of time-series data detected by the measurement unit 101. Groups consisting of the predetermined number of samples may be temporally consecutive or may be spaced at predetermined time intervals. According to the mean value calculation unit 105, the mean value of the obtained plurality of standard deviations is calculated. The activation evaluation unit 120 evaluates the activation of the biological samples on the basis of the mean value of the standard deviations. The activation evaluation unit 120 is provided with an activation calculation unit 108 and an activation classification unit 109. Therefore, according to the activation calculation unit 120, activation can be calculated based on the input information and can be classified by comparison with pre-stored information. The data display unit 110 displays the obtained activation. According to the apparatus, noise can be removed from digital signals (predetermined time-series data) captured at a fixed sampling rate, and then significant signals showing, for example, the opening and closing of ion channels can be extracted, measured and classified.

As shown in FIG. 9(B), the group SD calculation unit 102, the mean value calculation unit 105 and the activation evaluation unit 108 can be configured into a computer containing a hard disk on which programs for these calculations are recorded. The data display unit 110 can be a CRT display. As shown in FIG. 9(B), the computer is further provided with a normal distribution approximation unit 103, a stimulation unit 104 and a mean value/half-width calculation unit 106, which will be described later.

Figure 10:
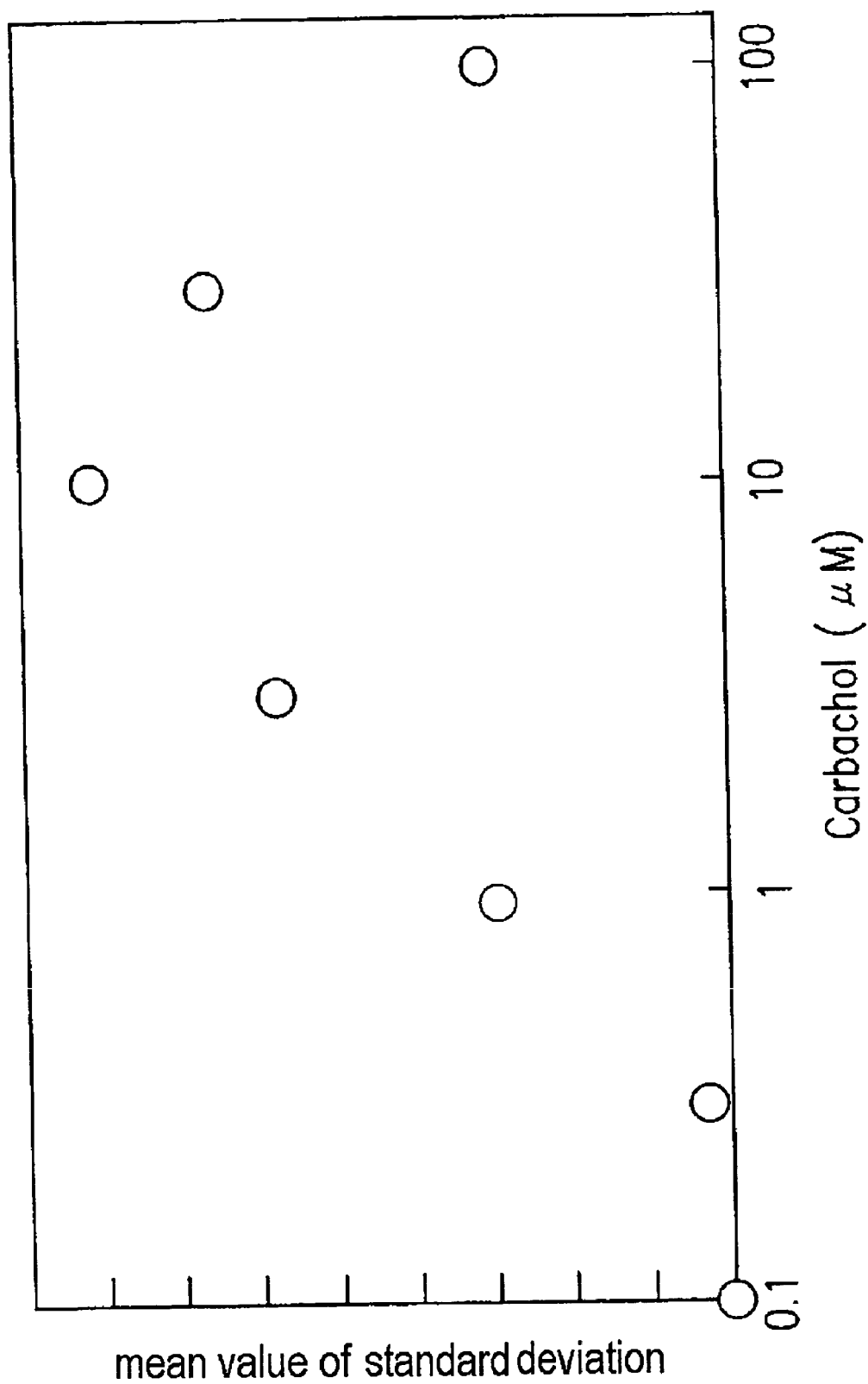
FIG. 10 shows the mean value variations of standard deviations for a Carbachol concentration.

The apparatus of this embodiment configured as described above was used to measure the effect of Carbachol, a chemical substance, on nerve cells prepared from lymnaea. Carbachol is known as an analog to the acetylcoline neurotransmitter. Carbachol (a product of Sigma Chemical Co.) was dissolved into an artificial brain-spinal fluid, and was subsequently caused to act on nerve cells at concentrations of 0, 0.1, 0.3, 1, 3, 10, 30 and 100 μM. Electrical signals emitted from the activated cells were then measured. For each Carbachol concentration, time-series data were sampled every 100 ms from 10-second time-series data obtained from the measurement unit 101, and standard deviations of the obtained data were calculated. FIG. 10 plots the mean values of the obtained standard deviations.

The mean value of the standard deviations represents variations in the electrical potential in the vicinity of the cell membrane, and is used for evaluating the activation of ion channels. As can be seen from FIG. 10, the mean value of the standard deviations increases with an increase in the Carbachol concentration, reaching its peak at the concentration of 10 μM, and then decreases. As described above, the measurement method and apparatus according to this embodiment verify that the activation of ion channels in the nerve cells of lymnaea depends on the Carbachol concentration. Moreover, the activation of all channels of the nerve cell can be inferred from the experiment results.

(Embodiment 4)

Figure 11:
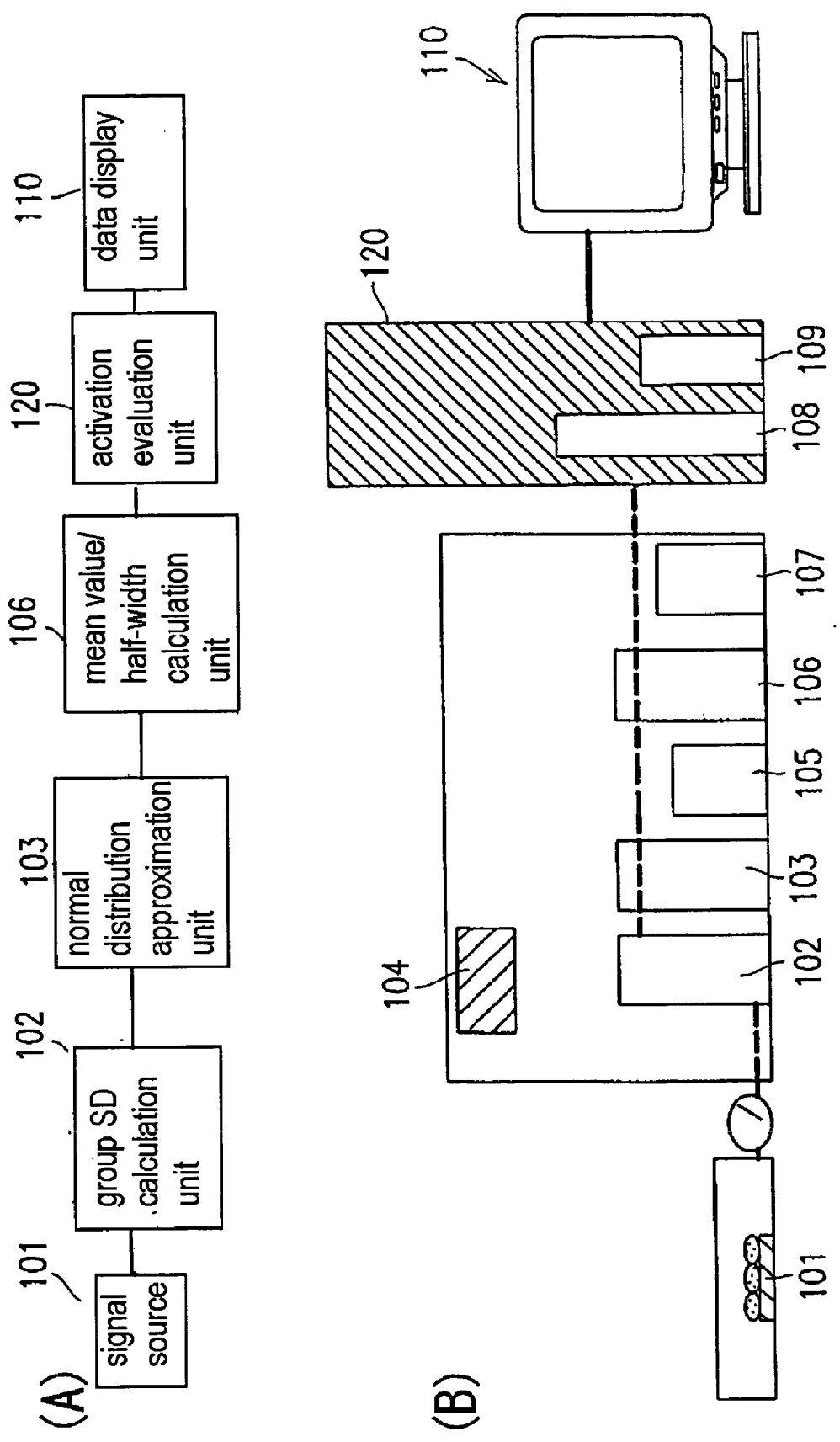
FIGS. 11(A) and (B) are block diagrams schematically illustrating an apparatus for measuring activity signals emitted from biological samples according to Embodiment 4 of the present invention.

FIG. 11 is a block diagram schematically illustrating a configuration of an apparatus for measuring the activity signals of biological samples according to Embodiment 4. As shown in FIG. 11(B), the apparatus is configured similarly to the apparatus of Embodiment 3 (see FIG. 9(B)). The mean value calculation unit 105 shown in FIG. 9(A) is not employed, whereas a normal distribution approximation unit 103 and a mean value/half-width calculation unit 106 are employed, resulting in a configuration as shown in FIG. 11(A).

The normal distribution approximation unit 103 classifies a plurality of standard deviations obtained in the group SD calculation unit 102 into a plurality of classes set at predetermined widths. The classes are plotted on the X axis and the number of standard deviations classified into each class is plotted on the Y axis, to obtain a graph. The graph obtained is approximated to a normal distribution. Methods for approximating the graph to a normal distribution include, for example, various curve fitting analyses, such as exponential decrease, exponential increase, Gaussian, Lorentzian, Sigma, Multipeak and non-linear methods. The mean value/half-width calculation unit 106 calculates the mean value and half-width (the half-peak height width) of the normal distribution obtained.

The apparatus of the present embodiment thus configured was used to measure how the chemical substance Carbachol acts on nerve cells prepared from lymnaea. More specifically, the normal distribution approximation unit 103 produced a frequency distribution of the standard deviations on the basis of signals that were detected by the measurement unit 101 before and after Carbachol was administered to lymnaea nerve cells at 50 μM concentration.

Figure 12:
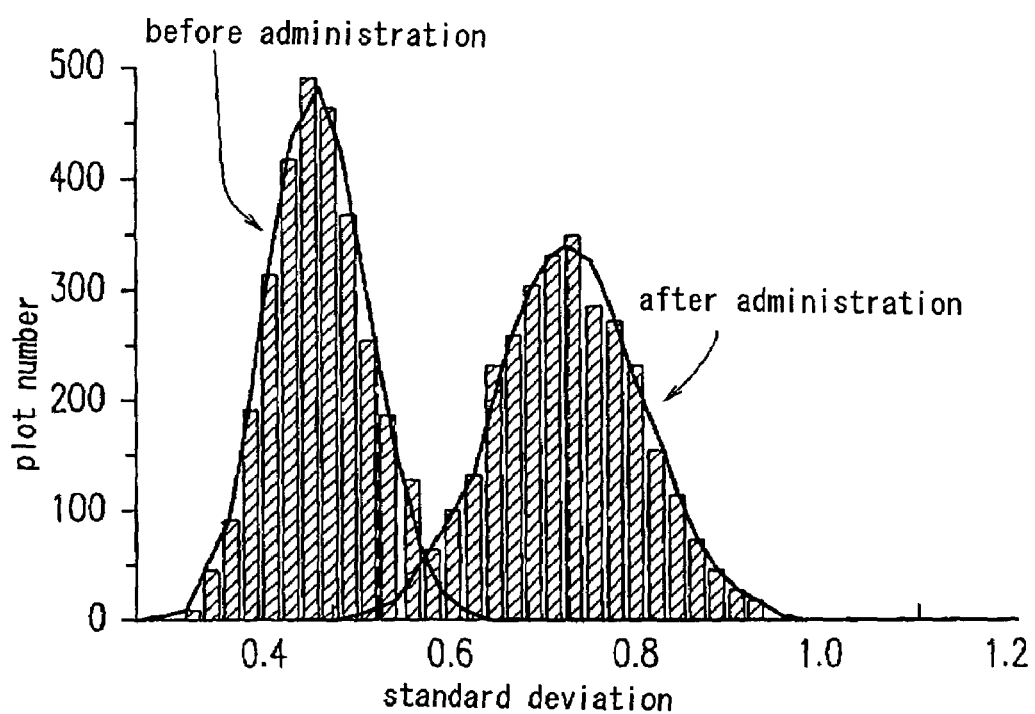
FIG. 12 shows the results obtained by approximating the standard deviation variations before and after the administration of Carbachol to a normal distribution.

FIG. 12 shows a histogram approximated to a normal distribution, where the histogram was produced from standard deviations obtained through calculations made every 5 ms based on time-series data from 10-second detection signals before and after the Carbachol is administered. The graph on the left shows the state before administration, and the graph on the right shows the state after administration. As shown in FIG. 12, the administration of Carbachol increases the mean value and half-width of the standard deviations. According to the calculation results of the mean value/half-width calculation unit 106, the mean value is 0.478 and the half-width is 0.109 before administration whereas the mean value is 0.703 and the half-width is 0.175 after administration. The calculation results show that the administration of Carbachol activates the ion channels of the nerve cells of lymnaea, and thus the fluctuations of the activity-related electrical potential caused by the opening and closing of the activated ion channels are expressed.

Figure 13:
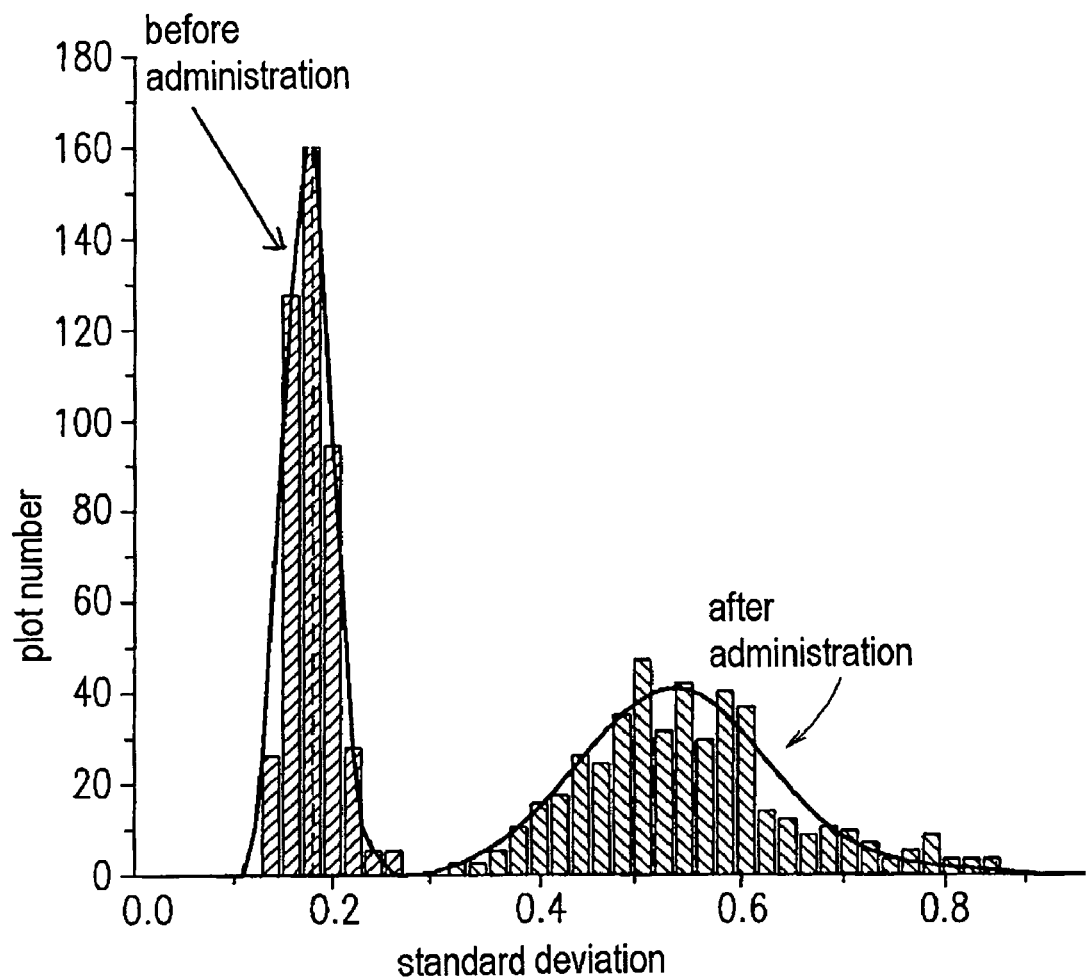
FIG. 13 shows the results obtained by approximating the standard deviation variations before and after the administration of Carbachol to a normal distribution according to a prior method.

FIG. 13 shows the results obtained by comparing cell conditions before administration and after administration by a prior intracellular recording method under the same conditions as in the above experiment. In this embodiment, an extracellular recording method is employed as a measurement method. A comparison of FIG. 12 with FIG. 13 indicates that the measurement results are the same between the intracellular recording method and the extracellular recording method. As described above, according to the measurement method of the present invention, the cell activities and variations thereof resulting from opening and closing of the ion channels can be measured easily without employing a prior intracellular recording method. Therefore, electrical variations in the biological sample can be measured even without forming a high-resistance seal (gigaseal) and the like between the biological sample and the measurement device, which eliminates the possibility of damaging the biological sample.

Furthermore, according to the present invention, the absolute values of ion channel activation and the increase or decrease of channel activation can be compared before and after the administration of a drug to a cell or with respect to the administration amount. As described later, for example, drug effects can be classified qualitatively and quantitatively.

(Embodiment 5)

The intracellular recording method verifies that activation of the Ca ion channels of smooth muscle cells is blocked depending on the concentration of nifedipine when stimulated by a 10-μM concentration of norepinephline. In this embodiment, a method for evaluating drugs using the apparatus for measuring the activity signals of biological samples according to the above Embodiment 4 will be described.

Figure 14:
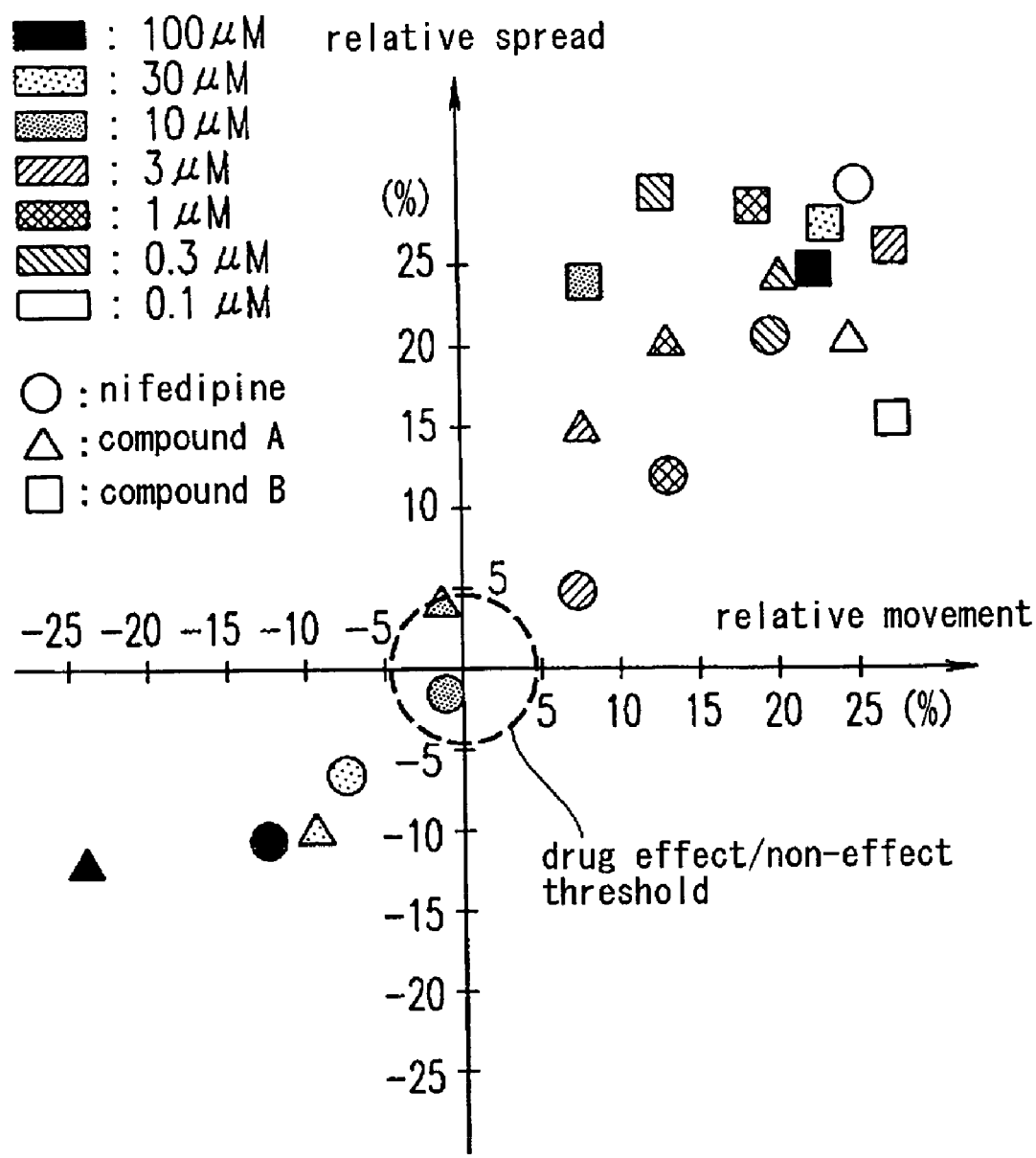
FIG. 14 shows the distances obtained by comparing the mean value and half-widths of an obtained normal distribution, respectively, with reference values.

FIG. 14 shows a normal distribution of standard deviations produced from detection signals of the measurement unit 101, illustrating distances obtained by comparing the mean values and half-widths of the normal distribution of standard deviations, respectively, with reference values. The distances are represented as relative movement and relative spread. The relative movement and relative spread of nifedipine at various concentrations (0.1 μM to 100 μM) were stored as parameters in a database in advance and then the effects of two types of Ca channel blocking agents, A and B are classified.

As shown in FIG. 14, the relative movement and relative spread behavior of compound A (Δ) are almost the same as those of nifedipine (○) at each concentration, and compound A is thus estimated to be the same kind of Ca ion channel blocking agent as nifedipine. In contrast, the relative movement and relative spread of compound B (□) scarcely vary even when the concentration varies, and compound B is remarkably different from nifedipine (○) in behavior. Therefore, compound (B) is a type of Ca ion channel blocking agent that does not exist in smooth muscle cells. In this way, the effects of various drugs can be estimated.

Furthermore, drug screening can be effectively conducted by determining whether or not the distance from the reference value is within a predetermined value (e.g., within a range of ±5% from the reference value, as shown by the dashed-line circle) based on the relative movement and relative spread shown in FIG. 14.

(Another Embodiment)

The present invention has been described with reference to the above embodiments, but it is not limited thereto. In the above Embodiments 4 and 5, for example, the distance obtained by comparing each of the mean value and the half-widths of the normal distribution obtained based on detection signals with the reference value is used for evaluation, but parameters based on the standard deviation (or variance) of the obtained normal distribution can also be suitably used to evaluate activity.

Figure 15:
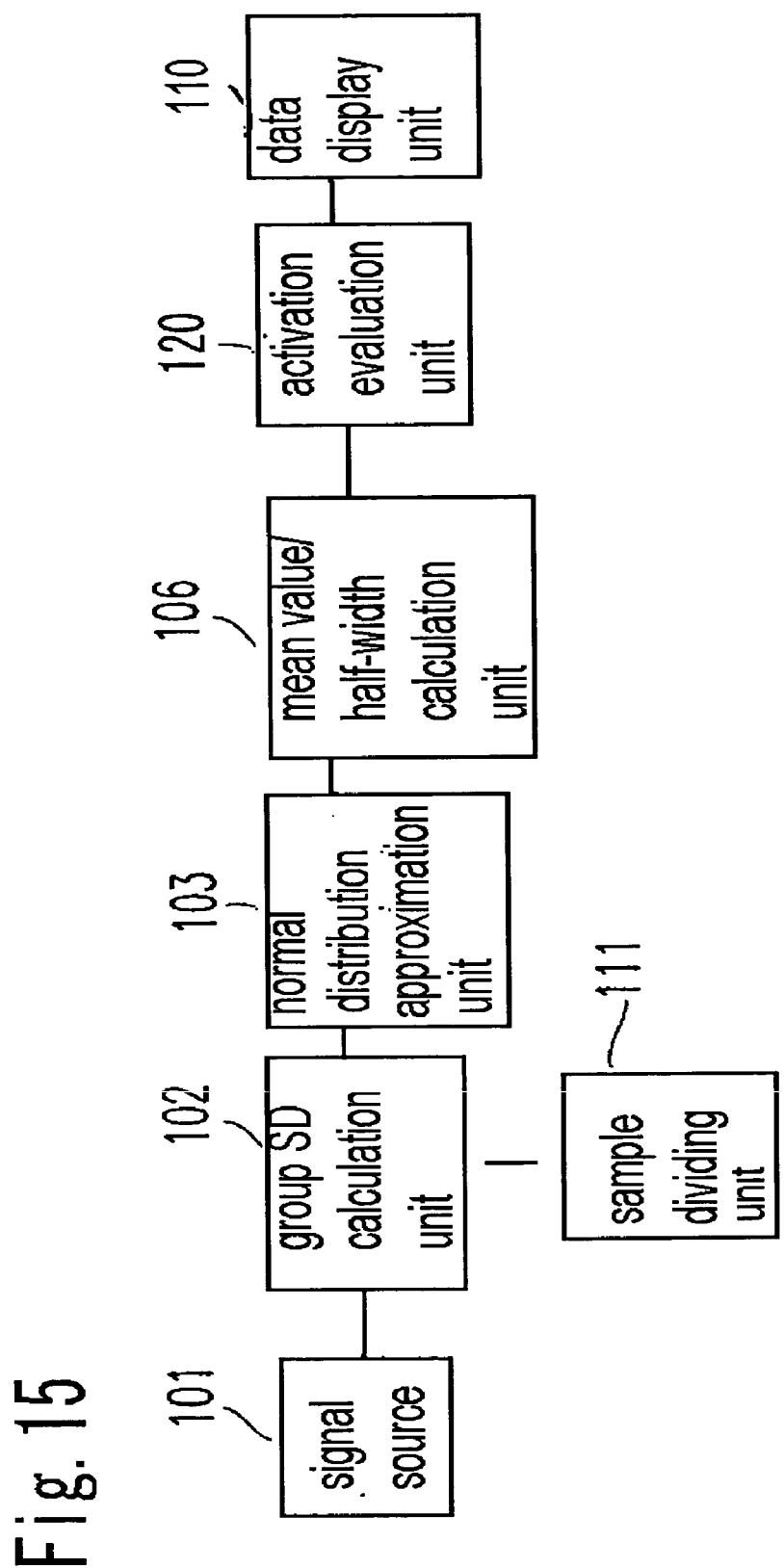
FIG. 15 is a block diagram schematically illustrating the configuration of an apparatus for measuring the activity signals of biological samples according to another embodiment of the present invention.

A configuration as shown in FIG. 15 can be obtained by further providing the configuration described in Embodiments 4 and 5 and shown in FIG. 11(A) with a sample dividing unit 111. The sample dividing unit 111 is a very effective means for analyzing the characteristics of various ion channels existing on the cell membrane.

Figure 16:
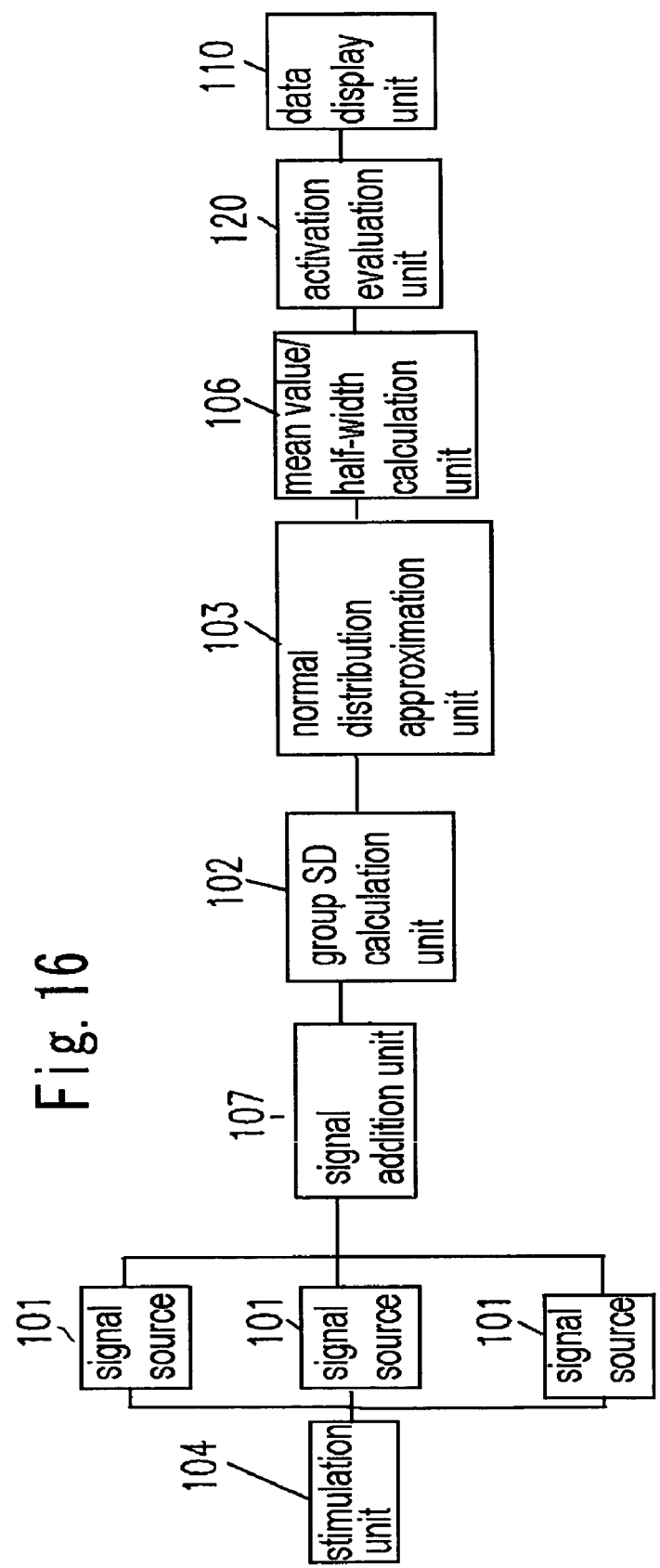
FIG. 16 is a block diagram schematically illustrating the configuration of an apparatus for measuring the activity signals of biological samples according to still another embodiment of the present invention.

In the configuration as described in Embodiments 4 and 5 and shown in FIG. 11(A), only one measurement unit (signal source) 101 is provided, whereas when a plurality of measurement electrodes 101 are provided as described in Embodiment 2, a configuration as shown in FIG. 16 can be obtained. In this measurement apparatus, a signal addition unit 107 adds the activity signals generated in the selected single or plural measurement units (signal sources) 101. When stimulation signals are provided to the respective signal sources 101 from a stimulation unit 104, biological samples can be simultaneously stimulated, which makes it possible to synchronize the timing of a plurality of activity signals to be added.

In each of the above embodiments, a suction line attachment is provided so as to suck the target liquid so that it passes through a porous insulating substrate. As a means of conveying the target liquid, however, a pressurizing apparatus can be provided instead of the suction line attachment so as to pressurize the measurement chamber, thus passing the target liquid through the porous insulating substrate.

In the above Embodiment 3, the mean value calculation unit calculates the mean value based on a plurality of standard deviations that are calculated by the group SD calculation unit 102. Alternatively, this plurality of standard deviations can be divided into groups using a specific constant in accordance with a time series and the mean value can be calculated per group. In the case where the mean value of each group increases along the time series, a data display unit may be configured so as to display the time that the mean value exceeds a predetermined value and/or the time that the rate of increase of the mean value falls below a predetermined value. This makes it possible to estimate the time lag until a chemical substance influences the cell activity.

INDUSTRIAL APPLICABILITY

As described above, the present invention provides an apparatus and a method for measuring activity signals emitted from biological samples, thus enabling activity signals emitted from biological samples to be detected easily, rapidly and accurately.

The present invention is applicable to high-speed medical screening or cell diagnosis (for example, discrimination between cancer cells and normal cells), and can be carried out on-site during a surgical operation.

The invention claimed is:

1. A method for measuring activity signals of a biological sample using a porous insulating substrate provided with a measurement electrode, the measurement electrode being arranged on a front surface of the porous insulating substrate, the method comprising the steps of:
- injecting a target liquid containing the biological sample into a measurement chamber;
- trapping the biological sample onto the measurement electrode provided on the front surface of the porous insulating substrate by conveying the target liquid from the measurement chamber and then passing the target liquid through the porous insulating substrate from the front surface to a back surface thereof to cause the biological sample to be adsorbed to the measurement electrode; and
- measuring activity signals of the biological sample through the measurement electrode.

2. A method for measuring activity signals of a biological sample according to claim 1, wherein the step of trapping the biological sample onto the measurement electrode comprises the step of sucking and then passing the target liquid through the porous insulating substrate.

3. A method for measuring activity signals of a biological sample according to claim 1, wherein the step of trapping the biological sample onto the measurement electrode comprises the step of conveying and discharging the entire target liquid stored in the measurement chamber; and said method further comprising the step of injecting a new target liquid containing a biological sample into the measurement chamber after the step of measuring activity signals of the previously injected target liquid, wherein measurement of activity signals of the new target liquid can be conducted by conveying the new target liquid from the measurement chamber.

4. A method for measuring activity signals of a biological sample according to claim 3, wherein the step of trapping the biological sample onto the measurement electrode further comprises the step of sucking the entire target liquid stored in the measurement chamber and then passing the entire target liquid through the porous insulating substrate.

5. A method for measuring activity signals of a biological sample according to claim 3, further comprising the step of replacing the porous insulating substrate before the step of injecting the new target liquid containing the biological sample to the measurement chamber and after the step of measuring activity signals of the previously injected target liquid.

6. A method for measuring activity signals of a biological sample according to claim 1, wherein the porous insulating substrate is composed of a resin film having a pore diameter of not less than 1 μm but not more than 1,000 μm and a thickness of not less than 1 μm but not more than 10,000 μm.

7. A method for measuring activity signals of a biological sample according to claim 1, wherein the porous insulating substrate is further provided with a conductor which is formed on at least one side via a mask layer and is electrically connected to the measurement electrode and the measurement electrode is infused into the porous insulating substrate more deeply than the conductor.

8. A method for measuring activity signals of a biological sample according to claim 7, wherein the measurement electrode and the conductor are formed by sputtering a conductive material onto the surface of the porous insulating substrate.

9. A method for measuring activity signals of a biological sample according to claim 1, wherein the step of injecting the target liquid into the measurement chamber further comprises the step of injecting the same or different type of target liquid separately to a plurality of measurement chambers; and the step of trapping the biological samples onto the measurement electrode further comprises the step of sucking the target liquid stored in the plurality of measurement chambers via a common suction line that communicates with the measurement chambers and then passing the target liquid through a porous insulating substrate, wherein at least one side of the porous insulating substrate is provided with a plurality of measurement electrodes corresponding to each of the measurement chambers, so that the same or different type of target liquid is simultaneously trapped onto each of the measurement electrodes.

10. A method for measuring activity signals of a biological sample according to claim 1, further comprising the steps of: calculating the standard deviation per a predetermined number of samples based on time-series data of the activity signals outputted via the measurement electrode; calculating the mean value of a plurality of the obtained standard deviations; evaluating activity of the biological samples based on the mean value of the obtained standard deviations; and displaying the results of the activity evaluation.

11. A method for measuring activity signals of a biological sample according to claim 1, further comprising the steps of: calculating the standard deviation per a predetermined number of samples based on time-series data of the activity signals outputted via the measurement electrode; classifying the obtained plurality of standard deviations into a plurality of classes set by a predetermined width and approximating the classification results to the normal distribution; evaluating activity of the biological samples based on the obtained normal distribution; and displaying the results of the activity evaluation.

12. A method for measuring the activity signals of a biological sample according to claim 11, wherein the step of evaluating activity further comprises the steps of: calculating the mean value and half-width of the obtained normal distribution; and evaluating activity based on the obtained mean value and half-width.

* * * * *

UNITED STATES PATENT AND TRADEMARK OFFICE
CERTIFICATE OF CORRECTION

PATENT NO.         : 7,172,860 B2                                         Page 1 of 1
APPLICATION NO.    : 10/678138
DATED              : February 6, 2007
INVENTOR(S)        : Hiroaki Oka et al.

It is certified that error appears in the above-identified patent and that said Letters Patent is hereby corrected as shown below:

On the title page,

Under section "(65)" insert section -- (30) Foreign Application Priority Data, 5/13/2002 (JP)............... 2002-137819 --

Signed and Sealed this

Twenty-fourth Day of July, 2007

JON W. DUDAS
*Director of the United States Patent and Trademark Office*